United States Patent [19]

Pastrone et al.

[11] Patent Number: 4,639,245
[45] Date of Patent: Jan. 27, 1987

[54] FLUID INFUSION PUMP DRIVER

[75] Inventors: Giovanni Pastrone, Los Gatos; Leland D. Chamness, Mountain View, both of Calif.

[73] Assignee: Oximetrix, Inc., Mountain View, Calif.

[21] Appl. No.: 811,262

[22] Filed: Dec. 20, 1985

[51] Int. Cl.$^4$ .............................................. A61M 5/20
[52] U.S. Cl. .................................. 604/152; 74/89.15; 128/DIG. 1; 417/413
[58] Field of Search ............................... 604/151-153; 417/413; 74/89.15; 128/DIG. 1

[56] References Cited

U.S. PATENT DOCUMENTS

| | | | |
|---|---|---|---|
| 3,156,236 | 11/1964 | Williamson | 128/DIG. 1 |
| 3,336,925 | 8/1967 | Thompson | 128/DIG. 1 |
| 3,985,133 | 10/1976 | Jenkins et al. | 604/152 |
| 4,089,624 | 5/1978 | Nichols et al. | 604/152 X |
| 4,396,385 | 8/1983 | Kelly et al. | 604/152 |
| 4,474,309 | 10/1984 | Solomon | 222/1 |

Primary Examiner—Dalton L. Truluck
Attorney, Agent, or Firm—Martin L. Katz; Robert W. Stevenson

[57] ABSTRACT

A fluid infusion pump driver device for pumping fluid from the chamber of a disposable cassette. The pump driver includes a reciprocatable plunger which is driven by a stepping motor. The motor and plunger are coupled through a universal joint which provides a threaded connection translating the incremental angular movements of the motor into incremental linear movements of the plunger, and the plunger is coupled directly to the frame through a flexible leaf spring to prevent wear in the threaded connection from generating undue noise or creating accuracy problems.

14 Claims, 3 Drawing Figures

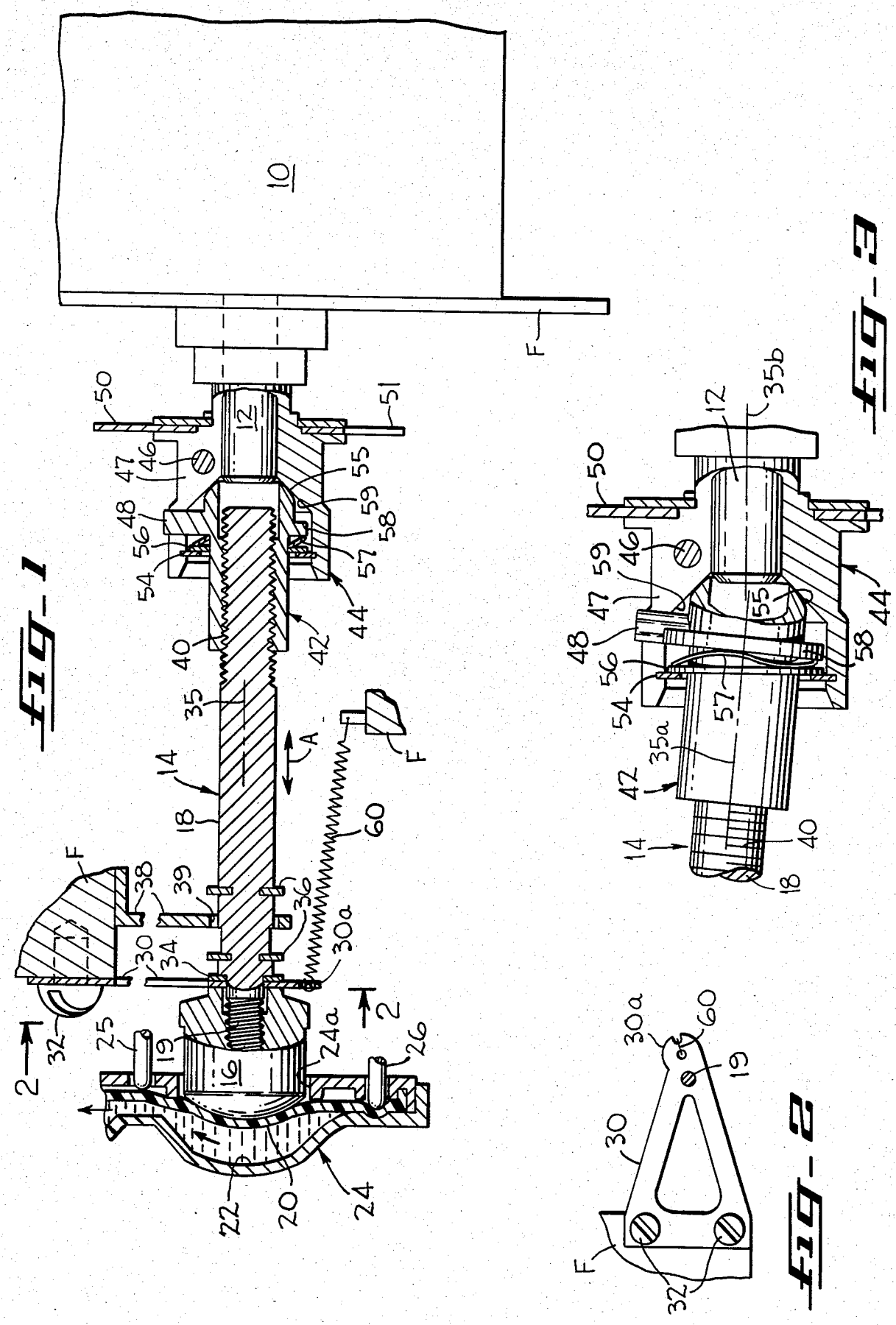

FLUID INFUSION PUMP DRIVER

BACKGROUND OF THE INVENTION

1. Field of the Invention

This invention relates to infusion pump driver devices adapted to pump fluid from disposable cassettes having pumping chambers formed therein from which fluid is displaced by a plunger or piston controlled by the driver device, and more particularly, it pertains to the driving plunger or piston arrangement for such pump driver devices.

2. Description of the Prior Art

In recent years, there has been a considerably increased use of positive displacement infusion pumping devices for delivering fluids intravenously or intra-arterially to patients in hospitals or other patient care locations. These have, to a large extent, replaced the time honored gravity flow control systems primarily due to their much greater accuracy in determining delivery rates and dosages, their relative sophistication in permitting a flexible and controlled feed from multiple liquid sources, and particularly, their ability to control with precision the amounts of dangerous drugs delivered to a patient over a given period of time.

A typical positive displacement fluid infusion pump system will be comprised of a pump driver device and a disposable cassette. The disposable cassette, which is adapted to be used only for a single patient and for one fluid delivery cycle, is typically a small plastic unit having an inlet and outlet adapted to be respectively connected through flexible tubing to the fluid supply container and to the patient receiving the infusion. The cassette will include a pumping chamber with the flow of fluid through the chamber being controlled by a plunger or piston activated in a controlled manner by the driver device. For example, the cassette chamber may have one wall thereof formed by a flexible diaphragm which is reciprocated by the plunger in the driver to cause fluid flow. The pump driver device may include primarily the plunger or piston for controlling the flow of fluid into and out of the pumping chamber in the cassette and it will also include all of the various electronics and control mechanisms to assure that the fluid is delivered to the patient at a pre-set rate, in a predetermined manner, and ony for a particular preselected time or total dosage. The pump driver device may also include pressure sensing and other liquid flow monitoring devices as well as valving members for opening and closing various passages in the cassette including the inlet and outlet passages of the pumping chamber.

One form of prior art fluid infusion pumping system is shown in U.S. Pat. No. 4,474,309 to Solomon wherein the cassete includes a pumping chamber which is controlled by a plunger extending from and actuated by the pump driver device through a stepping motor. The plunger, which is moved in a series of incremental movements during each liquid displacement stroke, is driven through a cam which translates the rotary motion of the stepping motor drive shaft to a linear plunger stroke. This cam type of drive inherently results in non-linear movements, and, in order to compensate, the incremental movements at the beginning and end of the plunge stroke, which are significantly smaller than the incremental movements during the major portion of the stroke, are utilized during the refill and initial catch-up phases of the pumping cycle so that relatively linear fluid delivery can be maintained over the major portion of the delivery phase.

U.S. Pat. No. 3,985,133 to Jenkins et al. and U.S. Pat. No. 4,396,385 to Kelly et al. both disclose infusion pump systems wherein the disposable cassette member thereof comprises a pumping chamber provided with a piston at one end and a three-way valve at the other end for selectively connecting the pumping chamber to the liquid supply container or to the liquid delivery tube, i.e., to the patient. The pump driver device includes a valve actuator member for activating the three-way valve in a controlled manner and a piston actuator member for providing a linear reciprocating drive movement to the piston. The piston actuator member is driven by a stepping motor within the pump driver device through a laterally offset connection threadedly secured to the motor drive shaft to translate the rotary movement of the motor drive shaft into linear movement of the actuator. While threaded connections between the drive motor and the infusion pump pistons or plungers have the advantage of uniform, precisely controlled incremental movements, they suffer the disadvantage in that wear between the contacting threaded members can result in a looseness in the drive which can give rise to errors or to a noisy operation which may be detrimental in the normal hospital environment.

SUMMARY OF THE INVENTION

With the infusion pump driver of the present invention, a plunger driver mechanism is provided which utilizes the accuracy of a threaded drive connection between the drive motor and the plunger but wherein the plunger is mounted through a pivotless member so that wear is very substantially reduced and consequent noise and accuracy problems are eliminated. Also, with a threaded drive connection between the motor and plunger, power consumption is reduced as compared to the prior art cam drive devices since no power is required to hold the plunger in place in the intervals between its incremental movements.

The infusion pump driver of the present invention generally comprises a motor with a drive shaft that is coupled to a plunger adapted to engage the flexible membrane in the disposable cassette member to pump liquid through the pumping chamber of the cassette in a precisely controlled manner. The plunger is secured to the frame of the driver so that generally linear movement thereof is permitted but rotational movement thereof is prevented. A special coupling means is provided permitting a threaded drive connection between the motor drive shaft and the plunger shaft but providing a universal coupling therebetween also so that relative pivotal movement between the motor drive shaft and the plunger shaft is readily accommodated.

BRIEF DESCRIPTION OF THE DRAWING

FIG. 1 is a longitudinal section through a portion of the infusion pump driver of the present invention showing the engagement of the pump driver plunger with a cassette pumping chamber.

FIG. 2 is a section taken along the line 2—2 of FIG. 1.

FIG. 3 is an enlarged longitudinal section of a portion of the mechanism of FIG. 1 showing the universal joint between the plunger shaft and the motor drive shaft with the axes of the shafts being unaligned.

DESCRIPTION OF A PREFERRED EMBODIMENT

FIG. 1 illustrates the reciprocatable plunger, the drive motor and various frame portions of the pump driver apparatus of the present invention. It will be recognized that the other portions of the pump driver apparatus, including the electronics and control mechanisms and the various sensor mechanisms and valve actuators, are not shown since such structure is more or less conventional and is, in any case, unrelated to an understanding of the present invention.

As shown in FIG. 1, a conventional stepping motor 10 is mounted upon the frame F of the pump driver apparatus and includes a drive shaft 12 projecting therefrom. The motor drive shaft is adapted to be connected to a plunger 14 comprised of a plunger head 16 and a shaft 18 securely connected to the head by means of a short threaded extension 19 on the end thereof. The plunger, which is adapted to be reciprocated in a generally linear direction (as shown by the arrow A), projects outwardly from the pump driver where it can engage a flexible diaphragm 20 forming one wall of the pumping chamber 22 within a disposable cassette 24 (only a portion of which is shown in FIG. 1). Liquid flow into and out of the cassette in the direction of the arrows is controlled by a pair of valve actuator members 25 and 26 which extend from the pump driver mechanism and are selectively actuated in the appropriate manner by means not shown and unrelated to the present invention.

It is an important feature of the present invention that the plunger 14 is attached to the frame F in a manner which permits generally linear travel of the plunger (in the direction of the arrow A) but which prevents rotation thereof so that a rotary drive connection between the plunger shaft 18 and the motor drive shaft 12 can be provided. In order to accomplish this, a triangularly shaped leaf spring 30 is provided (FIG. 2) for mounting the plunger. The broad end of the spring is rigidly secured to the frame F by means of a pair of spaced machine screws 32, and the lower, narrow end of the leaf spring is tightly clamped to the plunger shaft. As seen in FIG. 1, the plunger head 16 is tightened upon the plunger shaft extension 19 so as to force the leaf spring 30 into a flat engagement with a washer 34 secured against a shoulder portion of the plunger shaft 18. It will be recognized that as the plunger is reciprocated along the plunger shaft axis 35 (FIG. 1), the leaf spring 30 flexes and the rigid connection of the leaf spring with the frame F will displace the plunger shaft in a direction toward the fixed spring mounting plane at screws 32. However, this displacement will be quite slight even at the outer limits of the plunger stroke, and, since the plunger head 16 has sufficient clearance within the casstte wall opening 24a as shown in FIG. 1, the slight misalignment of the plunger head at the ends of the stroke will not create a problem.

The plunger shaft is also provided with a pair of stop rings 36 spaced apart along the length of the plunger shaft 18 and snap fitted into grooves on the shaft so as to project outwardly therefrom. A plate 38 is mounted to the frame F and has an aperture 39 through which the plunger shaft passes. As can be seen from FIG. 1, the aperture 39 permits the shaft 18 to freely pass but provide a stop when engaged by either of the projecting rings 36. These limit stop rings 36 thus provide the maximum range of travel of the plunger 14 and they will be used during the initial set-up of the plunger in order to properly locate the plunger so that its position can be accurately tracked. This latter function is accomplished by a flag disc 50 secured to the motor drive shaft 12 and having a slot 51 at one circumferential position thereon which can be tracked by conventional optical monitoring devices (not shown). It will be recognized that during normal operation of the apparatus, the full stroke of the plunger 14 will be well within the spacing between the stop rings 36 so that neither will be contacted by plate 38.

It is another important feature of the invention that the motor drive shaft 12 be connected with the plunger shaft 18 by a universal connection allowing free pivotal movement of the axes of the two shafts while also maintaining a snug threaded connection therebetween so that a fixed angular increment of rotation of the motor can be directly translated into a fixed linear travel distance of the plunger. As shown at the right-hand end of the apparatus of FIG. 1, and in detail in FIG. 3, the plunger shaft 18 is provided with external threads 40 at its distal end, and these threads are adapted to be received within the internal threads of a connector member 42. The connector member has a passage extending therethrough, including the threaded portion 40, for receiving the plunger shaft 18 and permitting relative rotary movement therebetween. A slotted or split collar 44 surrounds the connector member 42 and the distal end of the plunger shaft, such collar being tightly clamped to the end of the motor drive shaft 12 by means of a clamping bolt 46. The slot 47 provided in the collar, which permits the collar to be tightly clamped by the bolt 46 to the drive shaft, also serves to receive a laterally projecting key 48 of the connector member 42 so that the connector member is constrained to rotate with the collar and motor drive shaft 12. Since the connector member thus will rotate in incremental angular movements as the stepping motor drive shaft is driven, and since the plunger shaft 18 will be prevented from rotating due to the rigid connection of the leaf spring 30, the threaded connection 40 between the connector member 42 and the plunger shaft 18 causes the plunger to move in equal linear increments for each equiangular increment of drive by the stepping motor 10.

The previously mentioned flag disc 50 is secured to the collar 44 at the end thereof with the slot providing a means of detecting the particular position of the motor drive shaft (by means not shown) which can then be used in locating the plunger relative to the frame F by means of the stops 36. That is to say, the motor can be run to back the plunger up against one of the stops, and then can be run from the stop until the flag triggers a sensing mechanism, which point can be used as the starting position for the pumping stroke.

The connector member 42 in addition to providing a threaded connection between the drive shaft and the plunger shaft, also provides a universal connection—as particularly shown in FIG. 3. Thus, a spring clip 54 is secured within an internal groove in the enlarged outer end of the collar 44 and serves to secure within the collar a fixed washer 56 and a wavy washer 57 with the latter being adapted to abut a circumferentially projecting flange 58 on the connector member 42. The annular end surface 55 of the connector member is a spherical segment with a radius located on the axis of the connector member, and the inner surface 59 of the collar upon which the end surface 58 rides is conical so that the connector member can freely pivot about the axis of the collar. As is well shown in FIG. 3, the wavy washer 57 urges the connector member into engagement with the conical surface 59 of the collar but permits the axis 35a of the plunger shaft 18 to be rotated relative to the motor drive shaft axis 35b. Due to the fixed pivotal mounting of the end of the plunger by the leaf spring 30, this relative pivotal motion is necessary since the plunger shaft axis will be slightly displaced from the motor drive shaft axis, particularly at the ends of the pump stroke movement, even if it is precisely aligned in midstroke position as shown in FIG. 1. Also, this universal mounting permits the apparatus to overcome any slight misalignment in the parts when it is initially assembled.

Finally, in order to maintain the threaded connection between connector member 42 and the plunger shaft 18 secure and tight at all times, a tension spring 60 is connected between frame F and a projecting tab 30a of the leaf spring 30 (FIG. 2). This keeps the threads within threaded section 40 of the plunger shaft always in tight engagement and prevents any looseness which might create inaccuracies in the fluid delivery or the generation of intolerable noise.

It can be seen that with the plunger arrangement of the present invention, a plunger arrangement is provided wherein the plunger is pivotally fixed to the frame and connected to the motor drive shaft through a universal arrangement so that the accuracies of a threaded drive motion can be maintained without being saddled with the adverse effects that normally result from wear in the threaded connection.

Although the best mode contemplated for carrying out the present invention has been herein shown and described, it will be apparent that modification and variation can be made without departing from what is regarded to be the subject matter of the invention.

What is claimed is:

1. An infusion pump driver for pumping liquid from a cassette adapted to be selectively engaged with said driver and having a pumping chamber therein with an exposed wall thereof being formed by a flexible diaphragm, said driver comprising a frame structure, a motor mounted to said frame structure and including a drive shaft, a plunger adapted to engage said diaphragm for pumping liquid from the cassette pumping chamber, said plunger having an axially extending shaft, means for securing the plunger to said frame structure so as to permit movement thereof generally along the axis of the plunger shaft but preventing rotational movement thereof about said shaft axis, and means for coupling the plunger shaft to the drive shaft, said last named means providing a threaded connection between the drive shaft and the plunger shaft wherein rotation of the drive shaft results in movement of the plunger generally along the plunger shaft axis and including a universal joint for permitting relative pivotal movement between said plunger shaft axis and the axis of the drive shaft.

2. An infusion pump driver according to claim 1 wherein said means for securing the plunger to the frame structure comprises a leaf spring fixed to the frame at one end and to the plunger shaft at the other end so that movement of the plunger shaft generally along its axis causes the leaf spring to flex between its fixed connections.

3. An infusion pump driver according to claim 2 wherein said means for coupling the plunger shaft to the drive shaft includes a connector member threadedly connected to one end of the plunger shaft, and a universal mounting for securing the connector member to the motor driver shaft.

4. An infusion pump driver according to claim 3 wherein said universal mounting comprises a collar secured to the projecting end of the motor driver shaft, means for locking the connector member to the collar for joint rotary movement but permitting relative pivotal movement therebetween, and a spring positioned between the connector member and the collar for insuring tight engagement therebetween in their relative rotated positions.

5. An infusion pump driver according to claim 4 wherein said means for locking comprises a slot in said collar and a key projecting from said connector member and secured within said slot, said connector member being secured within said collar by the universal mounting spring so that it can freely axially pivot relative to the axis of the motor drive shaft.

6. An infusion pump driver according to claim 5 wherein said connector member is formed with a radially curved annulus at one end thereof and wherein said collar is provided with an inner conical surface adapted to receive the radially curved end surface of the connector member, said universal mounting spring maintaining said connector end surface and conical collar surface in continuous engagement while permitting rolling pivotal movement therebetween.

7. An infusion pump driver according to claim 3 further including a tension spring connected between said plunger and said frame structure for maintaining the threaded connection in continuous tight engagement.

8. In an infusion pump drivr for pumping liquid from a cassette adapted to be selectively engaged with said driver and having a pumping chamber therein with an exposed wall thereof being formed by a flexible diaphragm, said driver comprising a frame structure, a motor mounted to said frame structure and including a drive shaft, the improvement comprising a plunger adapted to engage said diaphragm for pumping liquid from the cassette pumping chamber, said plunger having an axially extending shaft, means for securing the plunger to said frame structure so as to permit movement thereof generally along the axis of the plunger shaft but preventing rotational movement thereof about said shaft axis, and means for coupling the plunger shaft to the drive shaft, said last named means providing a threaded connection between the drive shaft and the plunger shaft wherein rotation of the drive shaft results in movement of the plunger generally along the plunger shaft axis and including a universal joint for permitting relative pivotal movement between said plunger shaft axis and the axis of the drive shaft.

9. In an infusion pump driver according to claim 8 wherein said means for securing the plunger to the frame structure comprises a leaf spring fixed to the frame at one end and to the plunger shaft at the other end so that movement of the plunger shaft generally along its axis causes the leaf spring to flex between its fixed connections.

10. In an infusion pump driver according to claim 9 wherein said means for coupling the plunger shaft to the drive shaft includes a connector member threadedly connected to one end of the plunger shaft, and a universal mounting for securing the connector member to the motor drive shaft.

11. An infusion pump driver according to claim 10 wherein said universal mounting comprises a collar secured to the projecting end of the motor drive shaft, means for locking the connector member to the collar for joint rotary movement but permitting relative pivotal movement therebetween, and a spring positioned between the connector member and the collar for insuring tight engagement therebetween in their relative rotated positions.

12. In an infusion pump driver according to claim 11 wherein said means for locking comprises a slot in said collar and a key projecting from said connector member and secured within said slot, said connector member being secured within said collar by the universal mounting spring so that it can freely axially pivot relative to the axis of the motor drive shaft.

13. In an infusion pump driver according to claim 12 wherein said connector member is formed with a radially curved annulus at one end thereof and wherein said collar is provided with an inner conical surface adapted to receive the radially curved end surface of the connector member, said universal mounting spring maintaining said connector end surface and conical collar surface in continuous engagement while permitting rolling pivotal movement therebetween.

14. In an infusion pump driver according to claim 9 further including a tension spring connected between said plunger and said frame structure for maintaining the threaded connection in continuous tight engagement.

* * * * *